(12) United States Patent
Raposo et al.

(10) Patent No.: US 8,669,238 B2
(45) Date of Patent: Mar. 11, 2014

(54) USE OF KIF13A AND AP-1 INHIBITORS FOR INHIBITING MELANOGENESIS

(75) Inventors: Graca Raposo, Paris (FR); Cédric Delevoye, Paris (FR); Danièle Tenza, Survilliers (FR); Ilse Hurbain, Bures (FR)

(73) Assignees: Institut Curie, Paris Cedex (FR); Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 13/569,576

(22) Filed: Aug. 8, 2012

(65) Prior Publication Data

US 2012/0321575 A1 Dec. 20, 2012

Related U.S. Application Data

(62) Division of application No. 12/988,570, filed as application No. PCT/FR2009/050737 on Apr. 21, 2009, now abandoned.

(30) Foreign Application Priority Data

Apr. 22, 2008 (FR) ..................................... 08 52692
Apr. 22, 2008 (FR) ..................................... 08 52696

(51) Int. Cl.
  *A01N 43/04* (2006.01)
  *A61K 31/70* (2006.01)
  *A01N 63/00* (2006.01)

(52) U.S. Cl.
  USPC .......................... 514/44 A; 536/24.5; 435/455

(58) Field of Classification Search
  None
  See application file for complete search history.

(56) References Cited

U.S. PATENT DOCUMENTS

| | | |
|---|---|---|
| 2002/0128291 A1 | 9/2002 | Campochiaro et al. |
| 2002/0183399 A1 | 12/2002 | Kang et al. |
| 2004/0014700 A1 | 1/2004 | Kurfurst et al. |
| 2005/0074414 A1 * | 4/2005 | Tamarkin et al. ............... 424/47 |
| 2007/0031844 A1 | 2/2007 | Khvorova et al. |

FOREIGN PATENT DOCUMENTS

| | | | |
|---|---|---|---|
| EP | WO2008043561 | * 4/2008 | ............ A61K 48/00 |
| EP | 2 033 650 | 3/2009 | |
| WO | WO 01/58918 | 8/2001 | |
| WO | WO 01/89502 | 11/2001 | |
| WO | WO 01/98278 | 12/2001 | |
| WO | WO 2007/148697 | 12/2007 | |

OTHER PUBLICATIONS

Braun, V. et al. "AP-1 and ARF1 Control Endosomal Dynamics at Sites of FcR-mediated Phagocytosis" *Molecular Biology of the Cell*, Dec. 2007, pp. 4921-4931, vol. 18, XP-002509594.

Hirst, J. et al. "EpsinR: an ENTH Domain-containing Protein that Interacts with AP-1" *Molecular Biology of the Cell*, Feb. 2003, pp. 625-641, vol. 14, XP-002509595.

Nakagawa, T. et al. "A Novel Motor, KIF13A, Transports Mannose-6-Phosphate Receptor to Plasma Membrane through Direct Interaction with AP-1 Complex" *Cell*, Nov. 10, 2000, pp. 569-581, vol. 103, XP-002509746.

Valencia, J. C. et al. "Sorting of Pmel17 to melanosomes through the plasma membrane by AP1 and AP2: evidence for the polarized nature of melanocytes" *Journal of Cell Science*, 2005, pp. 1080-1091, vol. 119, XP-002509596.

Wonderlich, E. R. et al. "The Tyrosine Binding Pocket in the Adaptor Protein 1 (AP-1) μl Subunit is Necessary for Nef to Recruit AP-1 to the Major Histocompatibility Complex Class I Cytoplasmic Tail" *The Journal of Biological Chemistry*, Feb. 8, 2008, pp. 3011-3022, vol. 283, No. 6, XP-002571580.

* cited by examiner

*Primary Examiner* — Jennifer Pitrak McDonald
(74) *Attorney, Agent, or Firm* — Saliwanchik, Lloyd & Eisenschenk

(57) ABSTRACT

The present invention relates to novel pharmaceutical or cosmetic compositions comprising at least one inhibitor of a sub-unit of AP-1 adaptor complex, of a kinesin interacting with AP-1, in particular Kif13A, or of the interaction between a sub-unit of AP-1 adaptor complex and said kinesin, as well as the use of same to manufacture a drug intended for the treatment of pigmentary disorders and as a depigmentation agent.

21 Claims, 7 Drawing Sheets

SEQUENCE LISTING

<160> NUMBER OF SEQ ID NOS: 24

<210> SEQ ID NO 1
<211> LENGTH: 21
<212> TYPE: DNA
<213> ORGANISM: Artificial
<220> FEATURE:
<223> OTHER INFORMATION: sense Kif13A interfering RNA 1

<400> SEQUENCE: 1 ggcgggguagc gaaagaguat t                                      21

<210> SEQ ID NO 2
<211> LENGTH: 21
<212> TYPE: DNA
<213> ORGANISM: Artificial
<220> FEATURE:
<223> OTHER INFORMATION: antisense Kif13A interfering RNA 1

<400> SEQUENCE: 2
uacucuuucg cuacccgcca g                                       21

<210> SEQ ID NO 3
<211> LENGTH: 21
<212> TYPE: DNA

```
<213> ORGANISM: Artificial
<220> FEATURE:
<223> OTHER INFORMATION: sense Kif13A interfering RNA 2

<400> SEQUENCE: 3
gcaacaacuu gguaggaaat t                                              21

<210> SEQ ID NO 4
<211> LENGTH: 21
<212> TYPE: DNA
<213> ORGANISM: Artificial
<220> FEATURE:
<223> OTHER INFORMATION: antisense Kif13A interfering RNA 2

<400> SEQUENCE: 4
uuuccuacca aguuguugcg g                                              21

<210> SEQ ID NO 5
<211> LENGTH: 21
<212> TYPE: DNA
<213> ORGANISM: Artificial
<220> FEATURE:
<223> OTHER INFORMATION: sense mu1A (AP-1) interfering RNA 1

<400> SEQUENCE: 5
ggcaucaagu aucggaagat t                                              21

<210> SEQ ID NO 6
<211> LENGTH: 21
<212> TYPE: DNA
<213> ORGANISM: Artificial
<220> FEATURE:
<223> OTHER INFORMATION: antisense mu1A (AP-1) interfering RNA  1

<400> SEQUENCE: 6
ucuuccgaua cuugaugcct t                                              21

<210> SEQ ID NO 7
<211> LENGTH: 21
<212> TYPE: DNA
<213> ORGANISM: Artificial
<220> FEATURE:
<223> OTHER INFORMATION: sense Beta3A (AP-3) interfering RNA

<400> SEQUENCE: 7
ggcugaucuu gaagguuuat t                                              21

<210> SEQ ID NO 8
<211> LENGTH: 21
<212> TYPE: DNA
<213> ORGANISM: Artificial
<220> FEATURE:
<223> OTHER INFORMATION: antisense Beta3A (AP-3) interfering RNA

<400> SEQUENCE: 8
uaaaccuuca agaucagcct t                                              21

<210> SEQ ID NO 9
<211> LENGTH: 21
<212> TYPE: DNA
<213> ORGANISM: Artificial
<220> FEATURE:
<223> OTHER INFORMATION: sense control interfering RNA

<400> SEQUENCE: 9
uucuccgaac gugucacgut t                                              21
```

```
<210> SEQ ID NO 10
<211> LENGTH: 21
<212> TYPE: DNA
<213> ORGANISM: Artificial
<220> FEATURE:
<223> OTHER INFORMATION: antisense control interfering RNA

<400> SEQUENCE: 10
acgugacacg uucggagaat t                                             21

<210> SEQ ID NO 11
<211> LENGTH: 21
<212> TYPE: DNA
<213> ORGANISM: Artificial
<220> FEATURE:
<223> OTHER INFORMATION: sense mu1A (AP-1) interfering RNA 2

<400> SEQUENCE: 11
gcccuggguu cguuauauct t                                             21

<210> SEQ ID NO 12
<211> LENGTH: 21
<212> TYPE: DNA
<213> ORGANISM: Artificial
<220> FEATURE:
<223> OTHER INFORMATION: antisense mu1A (AP-1) interfering RNA 2

<400> SEQUENCE: 12
gauauaacgc acccagggct t                                             21

<210> SEQ ID NO 13
<211> LENGTH: 21
<212> TYPE: DNA
<213> ORGANISM: Artificial
<220> FEATURE:
<223> OTHER INFORMATION: sense mu1A (AP-1) interfering RNA 3

<400> SEQUENCE: 13
guggaucaaa cacaacaact t                                             21

<210> SEQ ID NO 14
<211> LENGTH: 21
<212> TYPE: DNA
<213> ORGANISM: Artificial
<220> FEATURE:
<223> OTHER INFORMATION: antisense mu1A (AP-1) interfering RNA 3

<400> SEQUENCE: 14
guuguugugu uugauccact t                                             21

<210> SEQ ID NO 15
<211> LENGTH: 21
<212> TYPE: DNA
<213> ORGANISM: Artificial
<220> FEATURE:
<223> OTHER INFORMATION: sense mu1A (AP-1) interfering RNA 4

<400> SEQUENCE: 15
ggcaucaagu aucggaagat t                                             21

<210> SEQ ID NO 16
<211> LENGTH: 21
<212> TYPE: DNA
<213> ORGANISM: Artificial
<220> FEATURE:
<223> OTHER INFORMATION: antisense mu1A (AP-1) interfering RNA 4
```

```
<400> SEQUENCE: 16
ucuuccgaua cuugaugcct t                                              21

<210> SEQ ID NO 17
<211> LENGTH: 21
<212> TYPE: DNA
<213> ORGANISM: Artificial
<220> FEATURE:
<223> OTHER INFORMATION: sense mu1A (AP-1) interfering RNA 5

<400> SEQUENCE: 17
cgaucagugu caaguucgat t                                              21

<210> SEQ ID NO 18
<211> LENGTH: 21
<212> TYPE: DNA
<213> ORGANISM: Artificial
<220> FEATURE:
<223> OTHER INFORMATION: antisense mu1A (AP-1) interfering RNA 5

<400> SEQUENCE: 18
ucgaacuuga cacugauccg g                                              21

<210> SEQ ID NO 19
<211> LENGTH: 21
<212> TYPE: DNA
<213> ORGANISM: Artificial
<220> FEATURE:
<223> OTHER INFORMATION: sense gamma-adaptin (AP-1) interfering RNA 1

<400> SEQUENCE: 19
accgaauuaa gaaguggut t                                               21

<210> SEQ ID NO 20
<211> LENGTH: 21
<212> TYPE: DNA
<213> ORGANISM: Artificial
<220> FEATURE:
<223> OTHER INFORMATION: antisense gamma-adaptin (AP-1) interfering
      RNA 1

<400> SEQUENCE: 20
accacuuucu uaauucggut t                                              21

<210> SEQ ID NO 21
<211> LENGTH: 21
<212> TYPE: DNA
<213> ORGANISM: Artificial
<220> FEATURE:
<223> OTHER INFORMATION: sense gamma-adaptin (AP-1) interfering RNA 2

<400> SEQUENCE: 21
ggcaugauga aagaauuact t                                              21

<210> SEQ ID NO 22
<211> LENGTH: 21
<212> TYPE: DNA
<213> ORGANISM: Artificial
<220> FEATURE:
<223> OTHER INFORMATION: antisense gamma-adaptin (AP-1) interfering
      RNA 2

<400> SEQUENCE: 22
guaauucuuu caucaugcct t                                              21

<210> SEQ ID NO 23
```

```
<211> LENGTH: 21
<212> TYPE: DNA
<213> ORGANISM: Artificial
<220> FEATURE:
<223> OTHER INFORMATION: sense gamma-adaptin (AP-1) interfering RNA 3

<400> SEQUENCE: 23
gguaaauggg aauaauauct t                                              21

<210> SEQ ID NO 24
<211> LENGTH: 21
<212> TYPE: DNA
<213> ORGANISM: Artificial
<220> FEATURE:
<223> OTHER INFORMATION: antisense gamma-adaptin (AP-1) interfering
      RNA 3

<400> SEQUENCE: 24
gauauuauuc ccauuuacct t                                              21
```

USE OF KIF13A AND AP-1 INHIBITORS FOR INHIBITING MELANOGENESIS

CROSS-REFERENCE TO RELATED APPLICATIONS

This application is a divisional of U.S. Ser. No. 12/988,570, filed Oct. 19, 2010 which is the U.S. national stage application of International Patent Application No. PCT/FR2009/050737, filed Apr. 21, 2009, the disclosures of which is hereby incorporated by reference in their entirety, including all figures, tables and amino acid or nucleic acid sequences.

The present invention relates to compositions that reduce the synthesis of melanic pigments in melanocytes and to uses of same.

TECHNOLOGICAL BACKGROUND OF THE INVENTION

In man, pigmentation results from the synthesis and distribution of melanic pigments most notably in the skin, the hair and the pigmentary epithelium of the iris. Thus, the color of the skin, the hair and the eyes depends principally on the types of pigments present and their concentrations. This pigmentation is regulated by many internal or external factors, such as, for example, exposure to ultraviolet radiation.

Melanins are macromolecules produced by melanocytes by the addition or condensation of monomers formed from tyrosine (eumelanin) or of tyrosine and cysteine (pheomelanin) The mechanism by which melanins are synthesized, or melanogenesis, is particularly complex and involves various enzymes, principally tyrosinase and the tyrosine related protein (tyrosinase-related protein-1 or Tyrp-1). During melanogenesis, these enzymes catalyze in particular the conversion of tyrosine into DOPA (dihydroxyphenylalanine) and then into dopaquinone. From this molecule, two metabolic pathways allow the synthesis of either eumelanin or pheomelanin.

Melanogenesis takes place in specialized intracellular organelles contained in melanocytes: melanosomes. Although melanosomes were among the first cellular organelles to be described morphologically (Seiji et al., 1963), their protein composition and their biogenesis remain relatively little-known.

Melanosome maturation can be broken down into four stages on the basis of morphological criteria. Stage I corresponds to a compartment delimited by a membrane with a variable quantity of intraluminal membranes. Stage II is an ellipsoidal structure with characteristic protein-like striations. These striations play an important role in melanin concentration, in the elimination of toxic synthesis intermediates and in facilitating the transfer of melanin to keratinocytes (Seiji et al., 1963). Melanin is detected from stage III by electron-dense deposits along the striations. Stage IV is an electron-dense structure in which the internal striations are no longer visible. This stage corresponds to the mature melanosome ready to be transferred to the keratinocytes (Van Den Bossche et al., 2006).

During the process of biogenesis, the "pigmented" mature melanosome (stages III and IV) is obtained by the addition of enzymes that are key to melanin synthesis and of effectors necessary to its transport toward the periphery (Raposo et al., 2001). The enzymes involved in melanogenesis are thus synthesized in the Golgi apparatus and then transferred in the pre-melanosomes. The mechanisms involved in this transfer are still relatively little-known. This type of transfer requires in particular the participation of adaptor protein (AP) complexes which are heterotetramers having the role of recruiting enzymes in the transport vesicles. There are four of these complexes, named AP-1 to AP-4. The inventors previously showed that AP-3 complex was involved in the transfer of tyrosinase toward melanosomes. However, a lack of AP-3 does not eliminate pigmentation and does not affect the transport of Tyrp-1. They also observed that AP-1 adaptor complex was able to interact with amino acid sequences of cytosolic domains of tyrosinase and Tyrp-1 without being able to elucidate the exact function of this complex in melanogenesis (Theos et al., 2005). Parallel to that, it was also shown that a kinesin, named Kif13A, was able to interact with a sub-unit of AP-1 (Nakagawa et al., 2000). This interaction was observed in cell lines lacking melanosomes. The existence of such an interaction in melanocyte cell lines, as well as its role in melanogenesis, has thus not been established.

Melanocyte dysfunction can lead to pigmentation anomalies. Hypopigmentation can result from depigmentation diseases, in particular albinism and vitiligo. Conversely, local hyperpigmentations can result from certain melanocyte conditions such as idiopathic melasma or benign melanocyte hyperactivity and proliferation causing, for example, senile pigmentary spots (senile lentigo). Hyperpigmentations can also be caused due to an accident, for example, by photosensitization or post-lesion scarring.

These hyperpigmentations can be treated by means of depigmentation substances administered by topical route. A depigmentation molecule acts on skin melanocytes and interferes with one or more stages of melanogenesis. Known depigmentation substances are in particular hydroquinone and its derivatives, ascorbic acid and its derivatives, placental extracts, kojic acid, arbutin, iminophenols (WO 99/22707), the combination of carnitine and quinone (DE 19806947), amino-phenol amide derivatives (FR 2772607), and benzothiazole derivatives (WO 99/24035).

These substances can present various disadvantages due in particular to their instability, the need for using them at high concentrations, their nonspecific action or their toxic, irritating or allergenic properties. Thus, effective and inoffensive depigmentation substances to treat or prevent hyperpigmentation by topical route are highly sought after in the fields of cosmetology and dermatology.

In the last few years, new approaches to treat diseases caused by melanocyte dysfunction have appeared. The use of antisense oligonucleotides was envisaged in particular. Indeed, document WO 99/25819 described oligonucleotides used to increase pigmentation by regulating the expression of tenascin to treat vitiligo and other depigmentation diseases and document FR 2804960 described antisense oligonucleotides to regulate the expression of tyrosinase or Tyrp-1 to treat hyperpigmentations.

SUMMARY OF THE INVENTION

The objective of the present invention is to provide novel depigmentation agents that are non-toxic, non-irritating and non-allergenic, that have a specific action on melanogenesis and that are stable in suitable formulations for administration by topical route.

The present invention concerns, firstly, a pharmaceutical or cosmetic composition comprising at least one inhibitor of kinesin interacting with AP-1 adaptor complex, in particular Kif13A, an inhibitor of a sub-unit of AP-1 adaptor complex, or an inhibitor of the interaction between a sub-unit of AP-1 adaptor complex or AP-1 complex and a kinesin interacting with AP-1 complex. In a first preferred embodiment of the invention, said inhibitor is an inhibitor of kinesin Kif13A. In a second preferred embodiment of the invention, said inhibitor is an inhibitor of a sub-unit of AP-1 adaptor complex. In a third preferred embodiment of the invention, said inhibitor is an inhibitor of the interaction between a sub-unit of AP-1 adaptor complex or AP-1 complex and a kinesin interacting with AP-1 complex, in particular kinesin Kif13A. In a particular embodiment, said inhibitor is a small molecule, an aptamer, an antibody, a nucleic acid or a dominant negative peptide. Preferably, said inhibitor is an aptamer, an antibody, a nucleic acid or a dominant negative peptide.

In a preferred embodiment, the present invention relates to a pharmaceutical or cosmetic composition comprising at least one nucleic acid comprising or consisting of a sequence capable of hybridizing specifically with a gene or mRNA coding for a sub-unit of AP-1 adaptor complex or for a kinesin interacting with AP-1 adaptor complex, in particular Kif13A, and to decreasing or suppressing expression of this protein. In a first preferred embodiment of the invention, said at least one nucleic acid comprises or consists of a sequence able to hybridize specifically with a gene or mRNA coding for a kinesin interacting with AP-1 adaptor complex, in particular Kif13A, and to decrease or suppress the expression of this protein. In a second preferred embodiment of the invention, said at least one nucleic acid comprises or consists of a sequence able to hybridize specifically with a gene or mRNA coding for a sub-unit of AP-1 adaptor complex and of decreasing or suppressing the expression of this protein. Preferably, said nucleic acid is an antisense oligonucleotide or iRNA, preferably siRNA. Said nucleic acid can have a sequence from 15 to 50 nucleotides, preferably from 15 to 30 nucleotides. In a preferred embodiment, said nucleic acid comprises a sequence selected among sequences SEQ ID Nos 1 to 6 and 11 to 24.

The composition can further comprise one or more other active substances, preferably selected among the group consisting of ellagic acid; arbutin; resorcinol; vitamin C; pantothenate; kojic acid; placental extracts; molecules interfering directly or indirectly with melanotropin (MSH), its receptor or adrenocorticotropic hormone (ACTH); polyols such as glycerin, glycol or propylene glycol; vitamins; keratolytic and/or exfoliation agents such as salicylic acid; alpha-hydroxy acids such as lactic acid or malic acid; ascorbic acid; retinoic acid; retinaldehyde; retinol; palmitate, propionate or acetate; anti-glycation and/or antioxidant agents such as tocopherol, thiotaurine, hypotaurine, aminoguanidine, thiamin pyrophosphate, pyridoxamine, lysine, histidine, arginine, phenylalanine, pyridoxine, adenosine triphosphate; anti-inflammatory agents; soothing agents and mixtures thereof; chemical or physical sun filters and deoxyribonucleic or ribonucleic acids, and derivatives of same. In a preferred embodiment, this composition is adapted for topical use.

In another aspect, the present invention relates to the use of a pharmaceutical or cosmetic composition according to the present invention for the preparation of a drug to treat or prevent a pigmentary disorder. In a preferred embodiment, the pigmentary disorder is hyperpigmentation.

In another aspect, the present invention relates to the use of a pharmaceutical or cosmetic composition according to the present invention as a cosmetic agent. Preferably, the cosmetic agent is a depigmentation agent.

DETAILED DESCRIPTION OF THE INVENTION

Figure 1A:
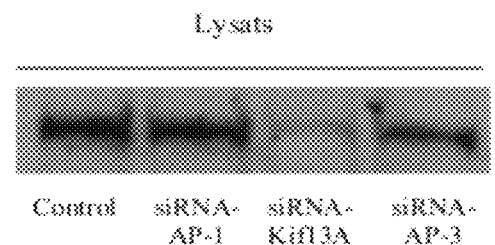
FIG. 1A presents the results obtained by western-blot experiments on cell lysates of melanocytes transfected with a siRNA-control, siRNA-AP-1 (μ1A), siRNA-AP-3 (β3A) or siRNA-Kif13A. The primary antibody used is anti-Kif13A.

The inventors showed, in a surprising way, that the synthesis of melanic pigments could be decreased by means of an inhibitor of a sub-unit of AP-1 adaptor complex or of an inhibitor of a kinesin interacting with AP-1, in particular by means of a nucleic acid blocking the expression of a sub-unit of AP-1 adaptor complex or of a kinesin interacting with AP-1 in melanocytes. They indeed observed that such a nucleic acid was not only able to disrupt the transport of melanogenesis enzymes of the Golgi apparatus toward the pre-melanosomes, thus blocking the maturation of these organelles, but also was able to decrease the expression of melanogenesis enzymes. The inventors thus revealed that this type of nucleic acid could decrease or inhibit the synthesis of melanin in melanocytes by acting on various stages of melanogenesis and thus constituted novel and particularly effective depigmentation agents.

The present invention concerns, firstly, a pharmaceutical or cosmetic composition comprising at least one inhibitor of a kinesin interacting with AP-1 adaptor complex, in particular Kif13A, an inhibitor of a sub-unit of AP-1 adaptor complex, or an inhibitor of the interaction between a sub-unit of AP-1 adaptor complex or AP-1 complex and a kinesin interacting with AP-1 complex.

The term "AP-1" used in this document refers to AP-1 adaptor complex which acts in the trans-Golgi network. It should not be confused with the transcription factor of the same name which consists of proteins coded by genes that are members of the jun and fos families. AP-1 adaptor complex is composed of 4 sub-units, γ, β1, α1 and µ1, and the inactivation of any one of these sub-units is sufficient to destabilize the complex and to render it inoperative (Braun, 2007).

In a first preferred embodiment of the invention, said inhibitor is an inhibitor of a kinesin interacting with AP-1, in particular kinesin Kif13A.

The present invention relates to any type of inhibitor of a kinesin interacting with AP-1, in particular Kif13A. The inhibitor can be any molecule able to decrease the activity or the expression of the kinesin. The inhibitor can be, without being limiting thereto, a small molecule, an aptamer, an antibody, a nucleic acid or a dominant negative peptide.

The term "small molecule" refers to a molecule of less than 1,000 daltons, in particular organic or inorganic compounds. The small kinesin-inhibiting molecules include, without being limiting thereto, acepromazine, chlorfenethazine, chlorpromazine, N-methyl chlorpromazine, cyamemazine, fluphenazine, mepazine, methotrimeprazine, methoxypromazine, norchlorpromazine, perazine, perphenazine, phenothiazine, prochlorperazine, promethazine, propiomazine, putaperazine, thiethylperazine, thiopropazate, thioridazine, trifluoperazine, triflupromazine as well as inhibiting molecules described in patent applications and patents WO 01/98278, WO 02/057244, WO 02/079169, WO 02/057244, WO 02/056880, WO 03/050122, WO 03/050064, WO 03/049679, WO 03/049678, WO 03/049527, WO 03/079973, U.S. Pat. No. 6,890,933, WO 2008/070739, WO 2006/060737, WO 2006/119146 and U.S. Pat. No. 6,777,200.

In an embodiment, the inhibitor is an aptamer, an antibody, a nucleic acid or a dominant negative peptide. As used here, the term "dominant negative peptide" refers to a peptide comprising at least one part of a kinesin interacting with AP-1 and able to suppress or decrease its activity. Preferably, the dominant negative peptide is only made up of the part of kinesin interacting with AP-1, i.e. the part corresponding to the tail of kinesin. This peptide is thus able to interact with AP-1 complex but, in absence of the segment corresponding to the head of kinesin, is unable to move along microtubules and thus to fulfill its function.

Several negative dominant peptides for kinesin Kif13A have already been described. In particular, a dominant negative peptide of Kif13A was obtained by expressing only the part of the Kif13A protein corresponding to the tail of the kinesin (Nakagawa et al., 2000).

In a preferred embodiment of the invention, the kinesin inhibitor is a nucleic acid comprising or consisting of a sequence capable of hybridizing specifically with a gene or mRNA coding for kinesin interacting with AP-1, in particular Kif13A, and to decrease or suppress the expression of this protein. Such nucleic acids are more amply detailed below.

In a second preferred embodiment of the invention, said inhibitor is an inhibitor of a sub-unit of AP-1 adaptor complex. The present invention relates to any type of inhibitor of one of the sub-units of AP-1 adaptor complex. By inhibitor of one of the sub-units of AP-1 adaptor complex is meant any molecule able to decrease the activity or the expression of one of the sub-units of AP-1 adaptor complex. The inhibitor can be, without being limiting thereto, a small molecule, an aptamer, an antibody, a nucleic acid or a dominant negative peptide. Preferably, the inhibitor is an aptamer, an antibody, a nucleic acid or a dominant negative peptide. In particular, the inhibitors of the γ and µ1 sub-units are preferred.

The term "small molecule" refers to a molecule of less than 1,000 daltons, in particular organic or inorganic compounds.

Several negative dominant peptides for a sub-unit of AP-1 adaptor complex have already been described. In particular, a negative dominant mutant of the µ1 sub-unit was obtained by introducing a mutation into the pocket binding tyrosine and is described in Wonderlich et al. (2008, J. Biol. Chem., vol. 283, 3011-3022).

The inhibitor can be a specific antibody of one of the sub-units of AP-1. Several of these antibodies are available commercially, for example specific antibodies of the γ sub-unit or β1 sub-unit (Sigma-Aldrich).

In the present application, inhibitor also means any molecule able to decrease or prevent the binding of a sub-unit of AP-1 adaptor complex to the other sub-units of the complex, i.e. any molecule able to decrease or prevent the formation of AP-1 complex. For example, the inhibiting molecule can be able to be bound to one of the sub-units of AP-1 and to cause a change of conformation preventing the binding of the aforesaid sub-unit to one or more of the other sub-units of AP-1 and thus to block the formation of AP-1 complex. It can also mask domains of interaction between the sub-units.

In a preferred embodiment of the invention, the inhibitor of AP-1 adaptor complex is a nucleic acid comprising or consisting of a sequence capable of hybridizing specifically with a gene or mRNA coding for a sub-unit of AP-1 adaptor complex and able to decrease or suppress the expression of this protein. Such nucleic acids are more amply detailed below.

In a third preferred embodiment of the invention, said inhibitor is an inhibitor of the interaction between a sub-unit of AP-1 adaptor complex or AP-1 complex and a kinesin interacting with AP-1 complex, in particular kinesin Kif13A. The present invention relates to any type of inhibitor of the interaction between a sub-unit of AP-1 adaptor complex or AP-1 complex and a kinesin interacting with AP-1 complex. Preferably, the kinesin is Kif13A. Preferably, the sub-unit of AP-1 is the β1 sub-unit. The tail of kinesin Kif13A interacts with the β1 sub-unit of AP-1 complex (Nakagawa et al., 2000). The inhibitor can be any molecule able to decrease or suppress the interaction between kinesin and AP-1 complex. The inhibitor can be, without being limiting thereto, a small molecule, an aptamer or an antibody. Preferably, the inhibitor is an antibody directed against the domain of the β1 sub-unit interacting with Kif13A or against the domain of the tail of the kinesin Kif13A interacting with the β1 sub-unit. The antibody is bound to one or the other of the molecules and thus blocks the interaction between Kif13A and AP-1 complex. In addition, the inhibitor could also be a decoy reproducing the domain of the β1 sub-unit interacting with Kif13A or the domain of the tail of the kinesin Kif13A interacting with the β1 sub-unit, this decoy competing with Kif13A or AP-1 for interaction between these two elements.

As used in the present invention, the term "antibody" includes monoclonal antibodies, chimeric antibodies, humanized antibodies, recombinant antibodies and fragments thereof. Antibody fragment means, for example, F(ab)2, Fab, Fab' or sFv fragments. In a particular embodiment, the antibody can be IgG, IgM, IgA, IgD or IgE, preferably IgG or IgM. Methods for producing antibodies are well known to those persons skilled in the art.

As used here, the term "aptamer" means a molecule of nucleic acid or a peptide able to bind specifically to a sub-unit of AP-1 complex or to a kinesin interacting with AP-1, in particular Kif13A. In a preferred embodiment, the aptamers are nucleic acids, preferably RNA, generally comprising between 5 and 120 nucleotides (Osborne et al., 1997). They can be selected in vitro according to a process known as SELEX (Systematic Evolution of Ligands by Exponential Enrichment).

In the present description, the terms "nucleic acid," "nucleic sequence," "polynucleotide," "oligonucleotide" and "nucleotide sequence" are used interchangeably and refer to a sequence of deoxyribonucleotides and/or ribonucleotides.

The term "iRNA" or "interfering RNA" used in this document refers to any RNA, simple or double strand, that interferes with a specific messenger RNA leading thus to its degradation and to a decrease in its translation into protein. This term includes small interfering RNA (siRNA), double-strand RNA (dsRNA), single-strand RNA (ssRNA), short hairpin RNA (shRNA), DNA-directed iRNA (ddiRNA) and microRNA (miRNA).

In this document, the term "hybridize" means that Watson-Crick hydrogen bonds can be established between the complementary bases to two strands of nucleic acid to form a duplex. In this document, the term "able to hybridize specifically" means that the nucleic acid used according to the invention is able to hybridize with a gene or a transcript coding for a sub-unit of AP-1 or a kinesin interacting with AP-1 under highly stringent hybridization conditions. Highly stringent hybridization conditions are widely described in the literature, for example in Sambrook et al., (1989), Maniatis et al., (1982 or one of their recent republications) and in Ausubel et al., (1995), and these conditions can be adapted by persons skilled in the art according to the size of the nucleotide fragments, according to suitable known techniques. On a purely illustrative basis, conditions of high stringency are advantageously as follows. Hybridization between two strands (in particular DNA-DNA, RNA-RNA or DNA-RNA) is carried out in two stages: (a) pre-hybridization at 42° C. for 3 hours in phosphate buffer (20 mm, pH 7.5) containing 5×SSC (1×SSC corresponds to a 0.15 M NaCl/0.015 M sodium citrate solution), 50% formamide, 7% sodium dodecyl sulfate (SDS), 10×Denhardt solution, 5% dextran sulfate and 1% salmon sperm DNA; (b) hybridization for 20 hours at a temperature depending on the size of the probe (for example, 42° C. for a probe of a size greater than 100 nucleotides) followed by two 20-minute washes at 20° C. with 2×SSC/2% SDS solution, a 20-minute wash at 20° C. with 0.1×SSC/0.1% SDS solution. The last wash is carried out with 0.1×SSC/0.1% SDS solution for 30 minutes at 60° C. for a probe longer than 100 nucleotides.

Within the context of the present invention, the term "gene coding for a sub-unit of AP-1 or a kinesin interacting with AP-1" is used to indicate the genomic sequence coding for one of the γ, β1, σ1 and μ1 sub-units of AP-1 or for a kinesin interacting with AP-1, in particular Kif13A. This term includes the 5' non-coding region, the region containing the initiation codon, the coding region and the 3' non-coding region of the gene. The term "gene coding for a sub-unit of AP-1" is used to indicate the genomic sequence coding for one of the γ, β1, σ1 and μ1 sub-units of AP-1. This term includes the 5' non-coding region, the region containing the initiation codon, the coding region and the 3' non-coding region of the gene. The term "gene coding for a kinesin interacting with AP-1" is used to indicate the genomic sequence coding for a kinesin interacting with AP-1, in particular Kif13A. This term includes the 5' non-coding region, the region containing the initiation codon, the coding region and the 3' non-coding region of the gene.

Within the scope of the present invention, the term "mRNA coding for a sub-unit of AP-1 or a kinesin interacting with AP-1" is used to indicate the ribonucleotide sequence resulting from the transcription of the gene coding for the corresponding protein. This term includes 3' and 5' untranslated regions (3'-UTR and 5'-UTR), exons and, optionally, unspliced introns. The term "mRNA coding for a sub-unit of AP-1" is used to indicate the ribonucleotide sequence resulting from the transcription of the gene coding for the corresponding protein. The term "mRNA coding for a kinesin interacting with AP-1" is used to indicate the ribonucleotide sequence resulting from the transcription of the gene coding for the corresponding protein. More particularly, the term "mRNA coding for kinesin Kif13A" is used to indicate the ribonucleotide sequence resulting from the transcription of the gene coding for kinesin Kif13A.

Genome sequences and proteins can be identified by their number in the GeneID database (http://www.ncbi.nlm.nih.gov/Genbank/index.html). Thus, the GeneID accession numbers for the γ, β1, σ1 and μ1 sub-units of AP-1 are, respectively, GeneID164, GeneID162, GeneID1174, GeneID8907 and the GeneID accession number for human kinesin Kif13A is GeneID63971.

The terms "melanin," "melanins" and "melanic pigments" are used interchangeably herein. They include the various pigments likely to be synthesized in melanosomes, including eumelanin or pheomelanin.

In this document, the term "pharmaceutical composition" refers to a composition according to the invention comprising a pharmaceutically acceptable carrier and/or excipient.

In this document, the term "cosmetic composition" refers to a composition according to the invention comprising a cosmetically acceptable carrier and/or excipient.

The term "depigmentation agent" refers in this description to an active agent able to inhibit or decrease the synthesis of melanin in melanocytes and thus to lighten the skin.

The inhibitors according to the invention are able, when they are introduced into a melanocyte, to induce decrease or suppression of the expression or activity of one or more sub-units of AP-1 or a kinesin interacting with AP-1, in particular Kif13A, or to induce decrease or suppression of the interaction of a sub-unit of AP-1 adaptor complex or AP-1 complex with a kinesin interacting with AP-1 complex, in particular kinesin Kif13A, with the consequence being a significant decrease in the synthesis of melanic pigments.

In a preferred embodiment, the nucleic acids used according to the invention are able, when they are introduced into a melanocyte, to induce decrease or suppression of the expression of one or more sub-units of AP-1 or a kinesin interacting with AP-1, in particular Kif13A, with the consequence being a significant drop in the synthesis of melanic pigments. In a particular embodiment, the nucleic acids used according to the invention are able, when they are introduced into a melanocyte, to induce decrease or suppression of the expression of one or more sub-units of AP-1, with the consequence being a significant drop in the synthesis of melanic pigments. In another particular embodiment, the nucleic acids used according to the invention are able, when they are introduced into a melanocyte, to induce decrease or suppression of the expression of a kinesin interacting with AP-1, in particular Kif13A, with the consequence being a significant drop in the synthesis of melanic pigments. These nucleic acids can act on the transcriptional or translational level.

By a "decrease" in expression is meant, for example, a decrease of 30%, 50%, 70%, 80%, 90% or 95% of the gene expression product.

The nucleic acids used according to the invention can be DNA, RNA or DNA/RNA chimera. They can be in single-strand or double-strand form or in a mixture of both. They can optionally comprise at least one modified or unnatural nucleotide such as, for example, a nucleotide comprising a modified base, such as inosine, methyl-5-deoxycytidine, dimethylamino-5-deoxyuridine, deoxyuridine, diamino-2,6-purine, bromo-5-deoxyuridine or any other modified base allowing hybridization. The nucleic acids used according to the invention can also be modified on the level of the internucleotide bonds such as, for example, phosphorothioates, H-phosphonates or alkyl-phosphonates, or on the level of the backbone such as, for example, alpha oligonucleotides, 2'-O-alkyl ribose or PNA (Peptide Nucleic Acid) (M. Egholm et al., 1992). These nucleic acids can be prepared by all methods known to those persons skilled in the art such as, for example, chemical synthesis, library screening, in vivo transcription or DNA recombination or amplification techniques.

In a particular embodiment of the invention, the nucleic acid can be a DNA that, when it is introduced into a cell, induces the production of interfering RNA (ddiRNA) that inhibit the expression of a target gene in the cell. This technology is known to those persons skilled in the art as DNA-directed interference RNA.

In another preferred embodiment, the nucleic acid is RNA, preferably interference RNA (iRNA). These RNA can be natural, synthetic or produced by techniques of recombination. They can also contain modified nucleotides or chemical modifications allowing them, for example, to increase their resistance to nucleases and thus to increase their lifespan in the cell. RNA interference is a phenomenon well known to those persons skilled in the art which makes it possible to specifically inhibit expression of the target gene at the post-transcriptional level. Many patents and patent applications have described the use of iRNA molecules to inhibit gene expression; examples include documents WO 99/32619, US 20040053876, US 20040102408 and WO 2004/007718. Preferably, the iRNA molecule is a molecule of siRNA, double stranded, of approximately 15 to 50 nucleotides in length, preferably approximately 15 to 30 nucleotides.

In an alternative embodiment of the present invention, the nucleic acid used to decrease or suppress the expression of a sub-unit of AP-1 or a kinesin interacting with AP-1, in particular Kif13A, is antisense nucleic acid. In a particular way, the nucleic acid used to decrease or suppress the expression of a sub-unit of AP-1 is antisense nucleic acid. In another particular way, the nucleic acid used to decrease or suppress the expression of a kinesin interacting with AP-1, in particular Kif13A, is antisense nucleic acid. This antisense nucleic acid can be complementary to all or part of a sense nucleic acid coding for a sub-unit of AP-1 or a kinesin interacting with AP-1. In a particular way, the antisense nucleic acid can be complementary to all or part of a sense nucleic acid coding for a sub-unit of AP-1. In another particular way, the antisense nucleic acid can be complementary to all or part of a sense nucleic acid coding for a kinesin interacting with AP-1. It can, for example, be complementary to mRNA. The antisense nucleic acid generally comprises a nucleotide sequence complementary to at least part of a transcript of a sub-unit of AP-1 or a kinesin interacting with AP-1, and hybridizes selectively to these transcripts by classic Watson-Crick interactions. In a particular way, the antisense nucleic acid generally comprises a nucleotide sequence complementary to at least part of a transcript of a sub-unit of AP-1. In another particular way, the antisense nucleic acid generally comprises a nucleotide sequence complementary to at least part of a transcript of a kinesin interacting with AP-1. The antisense inhibiting nucleic acid(s) can thus bind to transcripts of a gene coding for the $\gamma$, $\beta 1$, $\sigma 1$ and $\mu 1$ sub-units of AP-1 or coding for a kinesin interacting with AP-1 and, for example, block access to the cellular translation mechanism at the 5' end of the transcript of interest in the case of mRNA, impede its translation into protein, and enable suppression of expression of the transcript of interest in vivo (Kumar et al., 1993). In a particular way, the antisense inhibiting nucleic acid(s) can bind to the transcripts of a gene coding for the $\gamma$, $\beta 1$, $\sigma 1$ and $\mu 1$ sub-units of AP-1. In another particular way, the antisense inhibiting nucleic acid(s) can bind to the transcripts of a gene coding for a kinesin interacting with AP-1, in particular Kif13A. Such polynucleotides have been described, for example, in patent EP 0092574. Preferably, the antisense nucleic acid is complementary to mRNA coding for a sub-unit of AP-1 or for a kinesin interacting with AP-1, in particular Kif13A. In a particular way, the antisense nucleic acid is complementary to mRNA coding for a sub-unit of AP-1. In another particular way, the antisense nucleic acid is complementary to mRNA coding for a kinesin interacting with AP-1, in particular Kif13A. When the inhibiting nucleic acid is the antisense type, it can cover all or part of the sequence coding the transcript of interest, or all or part of the 3' or 5' non-coding sequence. Preferably, the antisense inhibiting nucleic acid is complementary to the ribosome binding sequence and the translation initiation sequence. The inhibiting nucleic acid generally has a length of at least 10 ribonucleotides, for example, 10, 15, 20, 25, 30, 35, 40, 45 or 50 ribonucleotides in length, preferably 15 to 30 ribonucleotides in length.

An antisense nucleic acid used according to the invention can be synthesized by methods of chemical synthesis or by recombinant DNA techniques known to those persons skilled in the art. The antisense DNA or RNA can in particular be synthesized chemically, produced by in vitro transcription of linear templates (for example, by PCR) or circular templates (for example, from viral or non-viral vectors), or can be produced by transcription in vivo from viral or non-viral vectors. Antisense nucleic acids can be modified to increase their stability, their resistance to nucleases, their specificity or their pharmacological properties. For example, an antisense nucleic acid can comprise modified nucleotides used to increase the stability of the duplex formed between the sense and antisense nucleic acids.

In another embodiment, the inhibiting nucleic acid is a ribozyme. Ribozymes are catalytic RNA molecules which have ribonuclease activity and are thus able to cleave single-strand nucleic acids, such as mRNA to which they are complementary. Specific ribozymes of transcripts coding for a sub-unit of AP-1 or a kinesin interacting with AP-1 can be designed, synthesized and produced according to methods well known to those persons skilled in the art (see, for example, Fanning and Symonds, 2006). The ribozyme generally has two distinct regions. A first region which has a certain specificity for the transcript of interest, that of a gene coding for a sub-unit of AP-1 or a kinesin interacting with AP-1 which can thus bind to the latter, whereas the second region confers on the ribozyme its catalytic activity of cleavage, ligation and splicing of the transcript of interest. In a particular way, the first region has a certain specificity for the transcript of interest, that of a gene coding for a sub-unit of AP-1. In another particular way, the first region has certain specificity for the transcript of interest, that of a gene coding for a kinesin interacting with AP-1, in particular Kif13A. Various types of ribozymes can be used such as, for example, hammerhead ribozymes or circular ribozymes, hairpin ribozymes or lasso ribozymes.

The interfering RNA or the antisense nucleic acids used according to the invention can be administered in the form of precursors or DNA molecules coding for them.

The nucleic acid used according to the invention generally has a length of 15 to 50 nucleotides, preferably from 15 to 30 nucleotides in length.

In the present invention, the nucleic acid is capable of hybridizing specifically to a gene or transcripts coding for a sub-unit of AP-1 complex or a kinesin interacting with AP-1, in particular Kif13A. In an embodiment, the nucleic acid is capable of hybridizing specifically to a gene or transcript coding for a sub-unit of AP-1 complex. In another embodiment, the nucleic acid is capable of hybridizing specifically to a gene or transcript coding for a kinesin interacting with AP-1, in particular Kif13A. Nevertheless, it is understood that the nucleic acid according to the invention does not need to have 100% complementarity with the target sequence to hybridize specifically. In particular, a nucleic acid with a degree of complementarity at least equal to approximately 90% is capable of hybridizing specifically. Preferably, the degree of complementarity between the nucleic acid of the invention and the target sequence is equal to 95%, 96%, 97%, 98%, 99% or 100%.

In a preferred embodiment, the nucleic acid used according to the invention comprises or consists of one or more sequences capable of hybridizing specifically with a gene or mRNA coding for a sub-unit of AP-1 adaptor complex or for kinesin Kif13A. Preferably, the nucleic acid comprises or consists of one or more sequences selected among sequences SEQ ID Nos 1 to 6 and 11 to 24. In a particular embodiment, the nucleic acid used according to the invention comprises or consists of one or more sequences capable of hybridizing specifically with a gene or mRNA coding for a sub-unit of AP-1 adaptor complex. Preferably, the nucleic acid comprises or consists of one or more sequences chosen among sequences SEQ ID Nos 5, 6 and 11 to 24. More preferably, the nucleic acid comprises or consists of one or more sequences capable of hybridizing specifically with a gene or mRNA coding for the µ1A or γ-adaptin sub-unit of AP-1. In another particular embodiment, the nucleic acid used according to the invention comprises or consists of one or more sequences capable of hybridizing specifically with a gene or mRNA coding for kinesin Kif13A. Preferably, the nucleic acid comprises or consists of one or more sequences chosen among sequences SEQ ID Nos 1 to 4.

In a particularly preferred embodiment, the nucleic acid used according to the invention comprises or consists of a molecule of double-strand interfering RNA formed by one of the following pairs: SEQ ID Nos. 1 and 2, SEQ ID Nos. 3 and 4, SEQ ID Nos. 5 and 6, SEQ ID Nos. 11 and 12, SEQ ID Nos. 13 and 14, SEQ ID Nos. 15 and 16, SEQ ID Nos. 17 and 18, SEQ ID Nos. 19 and 20, SEQ ID Nos. 21 and 22 and SEQ ID Nos. 23 and 24. In a particular embodiment, the nucleic acid used according to the invention comprises or consists of a molecule of double-strand interfering RNA formed by one of the following pairs: SEQ ID Nos. 1 and 2 and SEQ ID Nos. 3 and 4. In another particular embodiment, the nucleic acid used according to the invention comprises or consists of a molecule of double-strand interfering RNA formed by one of the following pairs: SEQ ID Nos. 5 and 6, SEQ ID Nos. 11 and 12, SEQ ID Nos. 13 and 14, SEQ ID Nos. 15 and 16, SEQ ID Nos. 17 and 18, SEQ ID Nos. 19 and 20, SEQ ID Nos. 21 and 22 and SEQ ID Nos. 23 and 24.

The present invention relates to a pharmaceutical or cosmetic composition comprising at least one inhibitor of a sub-unit of AP-1 adaptor complex, an inhibitor of a kinesin interacting with AP-1 adaptor complex, in particular Kif13A, or an inhibitor of the interaction between a sub-unit of AP-1 adaptor complex or AP-1 complex and a kinesin interacting with AP-1 complex, in particular any inhibitor as defined in the present application.

In a preferred embodiment, the present invention relates to a pharmaceutical or cosmetic composition specifically comprising at least one nucleic acid comprising or consisting of a sequence able to hybridize specifically with a gene or mRNA coding for a sub-unit of AP-1 adaptor complex or for a kinesin interacting with AP-1 adaptor complex, in particular Kif13A, and to decrease or suppress the expression of this protein, as described in the present application. In a particular embodiment, the pharmaceutical or cosmetic composition comprises at least one nucleic acid comprising or consisting of a sequence able to hybridize specifically with a gene or mRNA coding for a sub-unit of AP-1 adaptor complex and to decrease or suppress the expression of this protein, as described in the present application. In another particular embodiment, the pharmaceutical or cosmetic composition comprises at least one nucleic acid comprising or consisting of a sequence able to hybridize specifically with a gene or mRNA coding for a kinesin interacting with AP-1 adaptor complex and to decrease or suppress the expression of this protein, as described in the present application. Preferably, the kinesin is kinesin Kif13A.

In a preferred embodiment, the composition is a pharmaceutical or cosmetic composition whose formulation is adapted to topical administration. The inhibitor used in the composition is present in an effective amount. According to the type of inhibitor used, an effective amount is a quantity that reduces or suppresses expression or activity of a sub-unit of AP-1 adaptor complex or of a kinesin interacting with AP-1 adaptor complex, in particular Kif13A, or reduces or suppresses interaction between a sub-unit of AP-1 adaptor complex or AP-1 complex and a kinesin interacting with AP-1 complex.

According to the preferred embodiment, where the inhibitor is a nucleic acid, the nucleic acid used in the composition is present in an effective amount, for example, ranging from 0.00001% to 10% and preferably from 0.0003% to 3% (w/w) of the total weight of the composition.

The term "effective amount" as used in the present application is a quantity of inhibitor used according to the invention enabling a significant decrease in the synthesis of melanin. In a preferred embodiment, the term "effective amount" as used in the present application is a quantity of nucleic acid used according to the invention enabling a significant decrease in the synthesis of melanin. This decrease can, in particular, result in a visible change in the color of the skin. This decrease can, for example, be 5%, 10%, 15%, 20%, 25%, 30%, 35%, 40%, 45% or 50% of the quantity of melanin present in untreated cells. It can be measured by one of the methods described in the examples or known to those persons skilled in the art.

The composition according to the invention can include several inhibitors of identical or different type and with identical or different targets. It can include inhibitors either of a sub-unit of AP-1 adaptor complex, or of a kinesin interacting with AP-1 adaptor complex, in particular Kif13A, or of the interaction between a sub-unit of AP-1 adaptor complex or AP-1 complex and a kinesin interacting with AP-1 complex. It can include inhibitors of similar nature (for example nucleic acids only) or different nature (for example aptamers, antibodies and/or nucleic acids). In a preferred embodiment, this composition can include several nucleic acids comprising a sequence able to hybridize specifically with a gene or mRNA coding for a sub-unit of AP-1 adaptor complex or for a kinesin interacting with AP-1 adaptor complex, in particular Kif13A, and to decrease or suppress the expression of this protein, as described in the present application. It can also include a combination of several inhibiting nucleic acids targeting either the same sub-unit of AP-1, or different sub-units of AP-1, or the same kinesin interacting with AP-1, or different kinesins interacting with AP-1. In a particular embodiment, the composition can include several nucleic acids comprising a sequence able to hybridize specifically with a gene or mRNA coding for a sub-unit of AP-1 adaptor complex and to decrease or suppress the expression of this protein, as described in the present application. It can also include a combination of several inhibiting nucleic acids targeting either the same sub-unit of AP-1, or different sub-units of AP-1. In another particular embodiment, the composition can include several nucleic acids comprising a sequence able to hybridize specifically with a gene or mRNA coding for a kinesin interacting with AP-1 adaptor complex, in particular Kif13A, and to decrease or suppress the expression of this protein, as described in the present application. It can also include a combination of several inhibiting nucleic acids targeting either the same kinesin interacting with AP-1, or different kinesins interacting with AP-1.

The composition according to the invention can further comprise one or more additional active substances aimed at reinforcing the desired effects, for example, ellagic acid; arbutin; resorcinol; vitamin C; pantothenate; acid kojic; placental extracts; molecules interfering directly or indirectly with melanotropin (MSH), its receptor or adrenocorticotropic hormone (ACTH); polyols such as glycerin, glycol or propylene glycol; vitamins; keratolytic and/or exfoliating agents such as salicylic acid; alpha-hydroxy acids such as lactic acid or malic acid; ascorbic acid; retinoic acid; retinaldehyde; retinol; palmitate, propionate or acetate; anti-glycation and/or antioxidant agents such as tocopherol, thiotaurine, hypotaurine, aminoguanidine, thiamin pyrophosphate, pyridoxamine, lysine, histidine, arginine, phenylalanine, pyridoxine, adenosine triphosphate; anti-inflammatory agents; soothing agents and mixtures thereof; chemical or physical sun filters and deoxyribonucleic or ribonucleic acids, and derivatives thereof.

The composition according to the invention can arise in any galenical form normally used for topical application, in particular in the form of an aqueous hydroalcoholic or oily solution, an oil in water or water in oil or multiple emulsion, an aqueous or oily gel, a liquid, pasty or solid anhydrous product, a dispersion of oil in a polymer phase such as nanospheres and nanocapsules or better ionic and/or non-ionic lipid vesicles as described in French patent FR 2534487.

In particular, the composition according to the invention can include at least one inhibitor, preferably an inhibiting nucleic acid, described in the present application, encapsulated in a liposome.

According to the present invention, "liposome" means the small vesicles manufactured artificially and made up of phospholipid layers, separated from each other by aqueous compartments. They have a structure very close to that of cell membranes, which enables them to merge with them while releasing the active ingredients that they contain. The liposomes of use according to the invention can be multilamellar liposomes or MLV (MultiLamellar Vesicles), small unilamellar liposomes or SUV (Small Unilamellar Vesicles), or large unilamellar liposomes or LUV (Large Unilamellar Vesicles). The liposome can also be a nonionic liposome whose wall does not consist of phospholipids but rather nonionic lipids.

The composition according to the invention can be more or less fluid and have the appearance of a white or colored cream, pomade, milk, lotion, serum, paste or foam. Optionally, it can be applied to the skin in the form of aerosol. It can also be provided in solid form, pulverulent or not, for example in form stick. It further can be provided as patches, pencils, brushes and applicators for local application on spots of the face or hands. It can be used as a skin-care product and/or a make-up product.

As would be expected, the composition according to the invention can also contain the usual adjuvants in the fields of dermatology and cosmetics, such as hydrophilic or lipophilic gelling agents, hydrophilic or lipophilic active ingredients, preservatives, antioxidants, solvents, perfumes, loads, filters, pigments, the odor absorbers and colorants. The quantities of these various adjuvants are those classically used in the related fields. These adjuvants, according to their nature, can be introduced into the oil phase, the aqueous phase, lipid vesicles and/or nanoparticles.

When the cosmetic or dermatological composition of the invention is an emulsion, the proportion of the oil phase can range from 5% to 80% by weight, and preferably from 5% to 50% by weight compared to the total weight of the composition. The oils, emulsifiers and co-emulsifiers used in the composition in emulsion form are selected among those classically used in the related field. The emulsifier and co-emulsifier are present in the composition in a proportion ranging from 0.3% to 30% by weight, and preferably from 0.5% to 20% by weight compared to the total weight of the composition.

Examples of oils usable in combination with the inhibitors according to the invention, in particular with the nucleic acid according to the invention, include mineral oils such as petrolatum jelly; oils of vegetable origin such as avocado oil or soya oil; oils of animal origin such as lanolin; synthetic oils such as perhydrosqualene; siliconated oils such as cyclomethicone and fluorinated oils such as perfluoropolyethers. Also of use as fatty matter are fatty alcohols like cetyl alcohol, fatty acids or waxes such as carnauba wax or ozokerite.

Examples of emulsifiers and co-emulsifiers usable in combination with the nucleic acids according to the invention include esters of fatty acid and polyethylene glycol such as PEG-20 stearate and esters of fatty acid and glycerin such as glyceryl stearate.

Examples of hydrophilic gelling agents usable in combination with the inhibitors, in particular the nucleic acids, according to the invention, include carboxyvinylic polymers (carbomer), acrylic copolymers such as acrylate/alkylacrylate copolymers, polyacrylamides, polysaccharides, natural gums and clays. As lipophilic gelling agents, modified clays such as bentones, metal salts of fatty acids, hydrophobic silica or polyethylenes can be used, for example.

The present invention further relates to the use of a composition according to the invention as a cosmetic agent. In a preferred embodiment, the cosmetic agent is a depigmentation agent.

The present invention relates to a pharmaceutical or cosmetic composition comprising at least one inhibitor of a sub-unit of AP-1 adaptor complex, an inhibitor of a kinesin interacting with AP-1 adaptor complex, in particular Kif13A, or an inhibitor of the interaction between a sub-unit of AP-1 adaptor complex or AP-1 complex and a kinesin interacting with AP-1 complex, for a use in the treatment of pigmentary disorders. According to a particular embodiment, the inhibitor can be, without being limiting thereto, a small molecule, an aptamer, an antibody, a nucleic acid or a dominant negative peptide.

In a preferred embodiment, the present invention relates to a pharmaceutical composition comprising at least one nucleic acid comprising a sequence able to hybridize specifically with a gene or mRNA coding for a sub-unit of AP-1 adaptor complex or for a kinesin interacting with AP-1 adaptor complex, in particular Kif13A, and to decrease or suppress the expression of this protein, for the treatment of pigmentary disorders. In a particular way, the present invention relates to a pharmaceutical composition comprising at least one nucleic acid comprising a sequence able to hybridize specifically with a gene or mRNA coding for a sub-unit of AP-1 adaptor complex and to decrease or suppress the expression of this protein, for the treatment of pigmentary disorders. In another particular way, the present invention relates to a pharmaceutical composition comprising at least one nucleic acid comprising a sequence able to hybridize specifically with a gene or mRNA coding for a kinesin interacting with AP-1 adaptor complex, in particular Kif13A, and to decrease or suppress the expression of this protein, for the treatment of pigmentary disorders.

The present invention also relates to the use of a pharmaceutical composition according to the invention for the preparation of a drug to treat or prevent a pigmentary disorder.

The present invention also has as subject-matter a cosmetic or pharmaceutical method of depigmentation and/or bleaching of the human skin or treatment or prevention of a pigmentary disorder consisting in applying to the skin to be depigmented a cosmetic or pharmaceutical composition according to the invention.

Pigmentary disorders to be treated can be hyperpigmentations or hypopigmentations. Local hyperpigmentations can result from certain melanocyte disturbances and are characterized by an accumulation of melanin. Pigmentary disorders to be treated can be hyperpigmentation such as, for example, idiopathic melasma (not associated with pregnancy or with taking oral contraceptives), melasma (also called chloasma or the mask of pregnancy), actinic lentigo (also called senile lentigo, senile spots, sun spots, age spots or lentigo), pigmentary after-effects from acne, post-inflammatory pigmentations due to an abrasion, a burn, a scar, dermatosis and/or contact allergy, meadows dermatitis, pigmentations due to poison ivy, freckles, nevi such as congenital giant nevus, Becker nevus or Spitz nevus. Hyperpigmentations can be genetically determined or of metabolic or drug-related origin. They can be caused by accident for example by photosensitization or post-lesion scarring. The pigmentary disorder can also be expressed as hypopigmentation, such as vitiligo. In a preferred embodiment, the pigmentary disorder to be treated is hyperpigmentation. Preferably, the hyperpigmentation is melasma, idiopathic melasma or senile lentigo.

In the case of hyperpigmentation, the purpose of the treatment is to depigment the hyperpigmented areas and thus to decrease or suppress the visible symptoms associated with these specific pigmentary disorders.

In the case of hypopigmentation, the purpose of the treatment can be to standardize the color of the skin by depigmenting the residual pigmented areas.

The purpose of prevention is, in the case of hyperpigmentation, to avoid the appearance of hyperpigmented areas and, in the case of hypopigmentation, to avoid the appearance of disparities of skin color.

The examples which follow are presented as illustrations and are not limiting.

EXAMPLES

Materials and Methods

Cells, Antibodies and Reagents

The human melanocyte cell line MNT-1 is maintained in culture as described previously (Raposo et al., 2001).

The antibodies used in this example are listed below:

Anti β-tubulin rabbit polyclonal antibody (ab6046, Abcam®);

Rabbit anti-μ1A (sub-unit of AP-1) polyclonal antibody (Dr. Linton Traub, University of Pittsburg);

Mouse anti-γ-adaptin monoclonal antibody (clone 100/3; SIGMA®);

Mouse anti-Tyrp1 monoclonal antibody (tyrosinase-related protein-1) resulting from the supernatant of culture TA99 (Mel-5) (American Type Culture Collection, Manassas, Va., USA);

Anti-tyrosinase polyclonal antibody (ab15175, Abcam®);

Anti-Pmel 17 monoclonal antibody (HMB50, Labvisio®);

Rabbit anti-Kif13A polyclonal antibody (Bethyl Laboratories, Montgomery, USA);

Rabbit polyclonal and mouse monoclonal anti-horseradish peroxidase (HRP) antibodies (Jackson Immunoresearch®); and, Rabbit anti-mouse antibody coupled with Texas Red (Invitrogen®).

The reagents other than the antibodies used in this example are listed below:

Protein-A coupled to colloidal gold particles (Utrecht University cellular microscopy center, the Netherlands);

Protein G Agarose (Invitrogen®, catalog reference 15920-010);

Kit for western blot containing NuPAGE Bis-Tris 4-12% gel, NuPAGE 3-8% Tris-Acetate gel, MES-SDS migration and transfer buffer (Invitrogen®);

ECL Kit "western blotting detection reagents" (Amersham®) for visualization of HRP activity on PVDF membranes (Millipore®);

Paraformaldehyde (PFA) and bovine serum albumin (BSA) (Sigma®);

Saponin (Carlo Erba Reagents®); and,

Medium for mounting fluorescence microscopy coverslips "ProLong® Gold Antifade Reagent" with DAPI (Invitrogen®).

Sequences of Interfering RNA

```
Sense Kif13A siRNA
                                        SEQ ID No. 1
GGCGGGUAGCGAAAGAGUA dTdT Antisense Kif13A siRNA
                                        SEQ ID No. 2
UACUCUUUCGCUACCCGCC dAdG Sense AP-1 μ1A siRNA
                                        SEQ ID No. 5
GGCAUCAAGUAUCGGAAGA dTdT Antisense AP-1 μ1A siRNA
                                        SEQ ID No. 6
UCUUCCGAUACUUGAUGCC dTdT Sense AP-3 (β3A) siRNA
                                        SEQ ID No. 7
GGCUGAUCUUGAAGGUUUA dTdT
```

-continued

Antisense AP-3 (β3A) siRNA
SEQ ID No. 8
UAAACCUUCAAGAUCAGCC dTdT sense control siRNA
SEQ ID No. 9
UUCUCCGAACGUGUCACGU dTdT antisense control siRNA
SEQ ID No. 10
ACGUGACACGUUCGGAGAA dTdT Sense γ-adaptin siRNA
SEQ ID No. 19
ACCGAAUUAAGAAAGUGGU dTdT Antisense γ-adaptin siRNA
SEQ ID No. 20
ACCACUUUCUUAAUUCGGU dTdT RNA Interference $1 \times 10^6$ cells were inoculated in a 10 cm culture dish for two days, and then washed twice with preheated PBS before being cultured in 4 ml of OptiMem medium (Invitrogen®) in an incubator for 40 min.

Solution A was obtained by mixing 10 µl of 20 µM siRNA with 840 µL of OptiMem medium and by incubating this mixture for 20 min at room temperature. Solution B was obtained by mixing 50 µL of Oligofectamine™ (Invitrogen®) with 150 µL of OptiMem medium and by incubating this mixture for 20 min at room temperature.

Solutions A and B were then mixed and left for 20 min at room temperature. Then, this mixture was deposited on the cells that had been kept in the incubator for 4 hours. 5 ml of complete medium with 40% fetal calf serum (FCS) were then added to the cells. 24 hours later, the cells were recovered and inoculated in 6-well plates at a concentration of $1.5 \times 10^5$ cells/well. This same protocol was repeated the following day by adapting volumes.

Western-Blot

Following RNA interference, the cells were washed twice with PBS, and then incubated with 200 µl of lysis buffer (50 mM Tris, 150 mM NaCl, 10 mM EDTA, 1% Triton, 1% protease inhibitor, pH 8) per well on ice for 15 min. The cells were then scraped off, centrifuged (15,000 rpm, 4° C.) and the supernatants were collected. The quantity of total proteins was measured by the BCA Protein Assay kit (Pierce). 10 gm of each supernatant were loaded on a gel and migration took place for 35 min at 200 V. The gel was then transferred to a PVDF membrane (Millipore®) for 1 hour at 30 V. Then, the membrane was saturated with PBS/0.1% Tween/5% BSA buffer for 1 hour at room temperature, incubated for 45 min with the primary antibody diluted in WB buffer (PBS/0.1% Tween), rinsed 3 times for 10 min with WB buffer, incubated for 45 min with the corresponding secondary antibody coupled with HRP diluted in WB buffer and rinsed 3 times for 10 min in WB buffer. HRP activity then was revealed using the ECL kit (western blotting detection reagents) (Amersham®).

Fluorescence Microscopy

The cells inoculated beforehand on glass coverslips ($0.5 \times 10^5$ cells/coverslip) were washed twice with preheated PBS and then fixed for 10 minutes in a solution of PBS/4% PFA. After two washes at room temperature with PBS, the excess PFA that had not reacted was neutralized by treatment with 50 mM Glycine/PBS for 10 minutes. The nonspecific binding sites were then saturated by two 3-minute washes with PBS supplemented with 2 mg/ml BSA and the cells were permeabilized with permeabilization buffer (PBS/2% BSA/0.05% Saponin). The coverslips were then put in contact with 25 µl of primary antibody diluted in permeabilization buffer for 45 minutes at room temperature and excess antibody was eliminated by two 3-minute washes with permeabilization buffer. The coverslips were then incubated for 45 minutes at room temperature with 25 µl of secondary antibody diluted in permeabilization buffer.

After two 3-minute washes with permeabilization buffer followed by a wash with PBS, the coverslips were mounted on microscope slides with 15 µl of mounting medium (Pro-Long® Gold Antifade Reagent with DAPI, Invitrogen®) to attenuate the loss of fluorescence at the time of the observation.

Immunoprecipitation

The melanocyte cells were cultivated in 75 cm² flasks until confluence, then lysed with lysis buffer (50 mM Tris, 150 mM NaCl, 10 mM EDTA, 1% Triton, 1% protease inhibitor, pH 7.3) for 20 min at 4° C. The cells were then scraped and centrifuged (15,000 rpm, 4° C.) and the supernatants were collected. Beads coupled with protein G agarose were washed in lysis buffer and 20 ml of these beads were incubated with the lysates for 1 h at 4° C. under rotation. The lysates were then centrifuged at 4,000 rpm and the supernatants were collected and then incubated with washed beads that had been incubated beforehand for 1 h with 1 µg rabbit antibody (Kif13A control) or mouse anti-CD9 antibody (AP-1 γ-adaptin control). Immunoprecipitation is then carried out by centrifuging the lysates at 4,000 rpm and by putting the supernatants in contact with 20 µl of washed beads incubated beforehand for 2 h at 4° C. under rotation with 1 µg of rabbit antibody (Kif13a control), anti-Kif13a antibody (Kif13a), mouse anti-CD9 antibody (AP-1 γ-adaptin control) or mouse anti-γ-adaptin antibody (AP-1 γ-adaptin). The lysates were then centrifuged at 4,000 rpm, the supernatants collected and loaded on a gel for western-blot analysis.

Electronic Microscopy

The melanocyte cells inoculated beforehand in 6-wells plates and treated with "control" siRNA and siRNA-Kif13A or siRNA-µ1A were fixed either with a mixture of 2% PFA and of 2% glutaraldehyde (conventional microscopy) or a mixture of 2% PFA and 0.5% glutaraldehyde (immunostaining) in a 0.2 M pH 7.4 phosphate buffer for 4 hours at room temperature.

Conventional microscopy: After several washes in a 0.2 M sodium cacodylate buffer, the cells were fixed with a 2% osmic acid ($OsO_4$) solution for 45 min. After rinsing with distilled water, the cells were dehydrated with increasing concentrations of ethanol and then coated in Epon 812 resin. After polymerization for 48 hours at 60° C., the ultrafine slices were taken, contrasted with 4% uranyl acetate for 5 min and then were observed under the electron microscope (Philips CM120, FEI Company®). Images were taken with a KeenView camera (SIS®, Germany).

Immunostaining: After several washes in a 0.2 M phosphate buffer containing 0.1 M glycine, the cells were prepared for ultracryomicrotomy as described previously in document by Raposo et al. (1997).

In short, the cell pellets were first coated in 10% gelatin. After solidification at 4° C., 1 mm³ blocks were cut and infused in 2.3 M sucrose for 2 h. The blocks of cells were frozen on their support and ultrafine frozen sections were taken with an ultracryomicrotome (Leica®, Austria). The sections recovered on electronic microscopy grids were immunostained with anti-Tyrp1 and anti-Pmel17 antibodies. These antibodies were visualized with protein A coupled to colloidal gold particles. The sections were contrasted and coated in a mixture of uranyl acetate and methyl cellulose before observation under the electron microscope (Philips CM120, FEI Company®). Images were taken with a KeenView camera (SIS®, Germany).

Quantification of Melanin

After RNA interference, the cells were washed twice in PBS and were incubated with 150 μl melanin buffer (50 mM Tris, 2 mM EDTA, 150 mM NaCl, 1% protease inhibitor, pH 7.4). They then were scraped and collection in a single fraction before being sonicated for 20 s at maximum intensity. 10 μl were then taken to quantify proteins (with BCA Protein Assay kit, Pierce) and 200 μg of protein were taken and centrifuged at 15,000 rpm for 15 min at 4° C. The supernatant was eliminated and the pellet washed with 500 μl of an ethanol/ether (1:1) solution. Lastly, the pellet was solubilized with 230 μl of a 2 M NaOh/20% DMSO solution at 55° C. Once solubilized, 200 μL were taken in order to measure optical density at 492 nm.

Quantification of White Cells

Quantification was carried out on cells prepared for immunofluorescence using an epifluorescence microscope. The cells were observed in phase contrast and the presence (black) or the absence (white) of pigmented mature melanosomes was quantified.

Example 1

Western-blot experiments on cellular lysates of melanocytes transfected with siRNA-AP-1 (μ1A), siRNA-Kif13A and siRNA-AP-3 (β3A) made it possible to show that the expression of Kif13A is not disrupted by inactivation of AP-1 or AP-3 (FIG. 1A). On the other hand, in melanocytes transfected with siRNA-Kif13A, the expression of Kif13A was completely suppressed (FIGS. 1A and 1C) whereas the expression of the μ1A sub-unit of AP-1 was not disrupted. These results thus show the effectiveness and the specificity of siRNA to inactivate this protein in melanocytes.

Figure 1B:
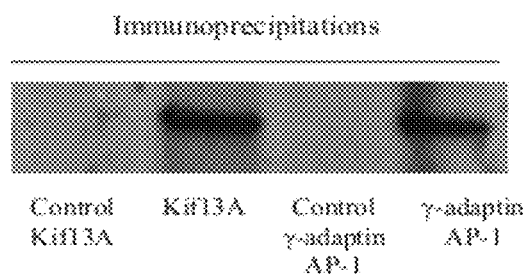
FIG. 1B presents the results of immunoprecipitations with anti-Kif13A antibody or anti-γ-adaptin antibody (AP-1) created from melanocyte cell lysates. The primary antibody used to visualize the western-blot is anti-Kif13A.
Figure 1C:
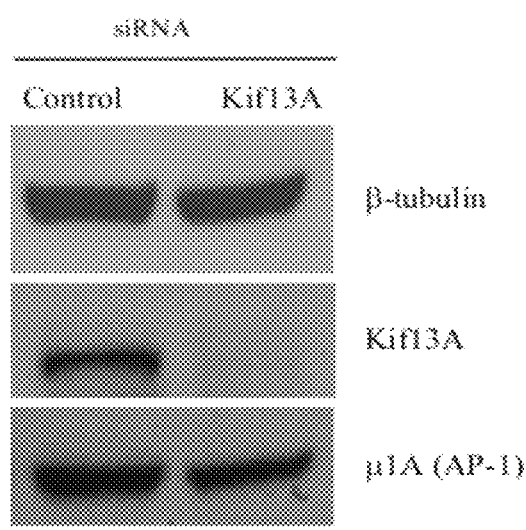
FIG. 1C presents the results obtained by western-blot experiments on protein extracts of melanocytes transfected with a siRNA-control or siRNA-Kif13A. The levels of expression of kinesin Kif13A and AP-1 complex sub-unit μ1A are evaluated here quantitatively by using the expression of β-tubulin as reference.

Moreover, immunoprecipitation experiments carried out on melanocytes made it possible to show that the Kif13A protein co-precipitates with the γ-adaptin AP-1 sub-unit and thus that the interaction between Kif13A and AP-1 observed previously in non-melanocyte cell lines (Nakagawa et al., 2000) also exists in melanocyte cell lines (FIG. 1B).

Figure 2:
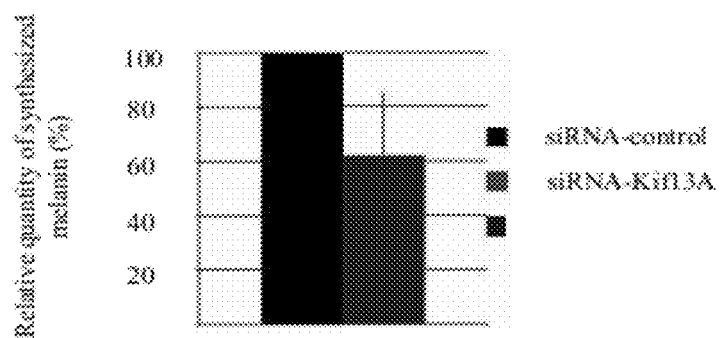
FIG. 2 shows a diagram presenting the percentage of melanin in melanocytes transfected with siRNA-control or siRNA-Kif13A. The quantity of melanin in melanocytes transfected with siRNA-control is regarded as being equal to 100%. The quantity of melanin was determined by measuring the optical density of the cell lysate at a wavelength of 492 nm.

The relative quantity of melanin in melanocytes transfected with siRNA-Kif13A compared to the quantity present in the cells transfected with siRNA-control was determined by measurement of the optical density of the cell lysate at a wavelength of 492 nm (FIG. 2). The results presented in FIG. 2 show that the use of siRNA-Kif13A made it possible to obtain a decrease in the quantity of synthesized melanin of about 40% compared to the cells transfected with siRNA-control.

Observations under electronic microcopy were made on melanocytes transfected with siRNA-Kif13A or siRNA-control either in conventional electronic microscopy (FIG. 3) or with immunostaining with anti-Tyrp1 antibodies (data not shown).

Figure 3:
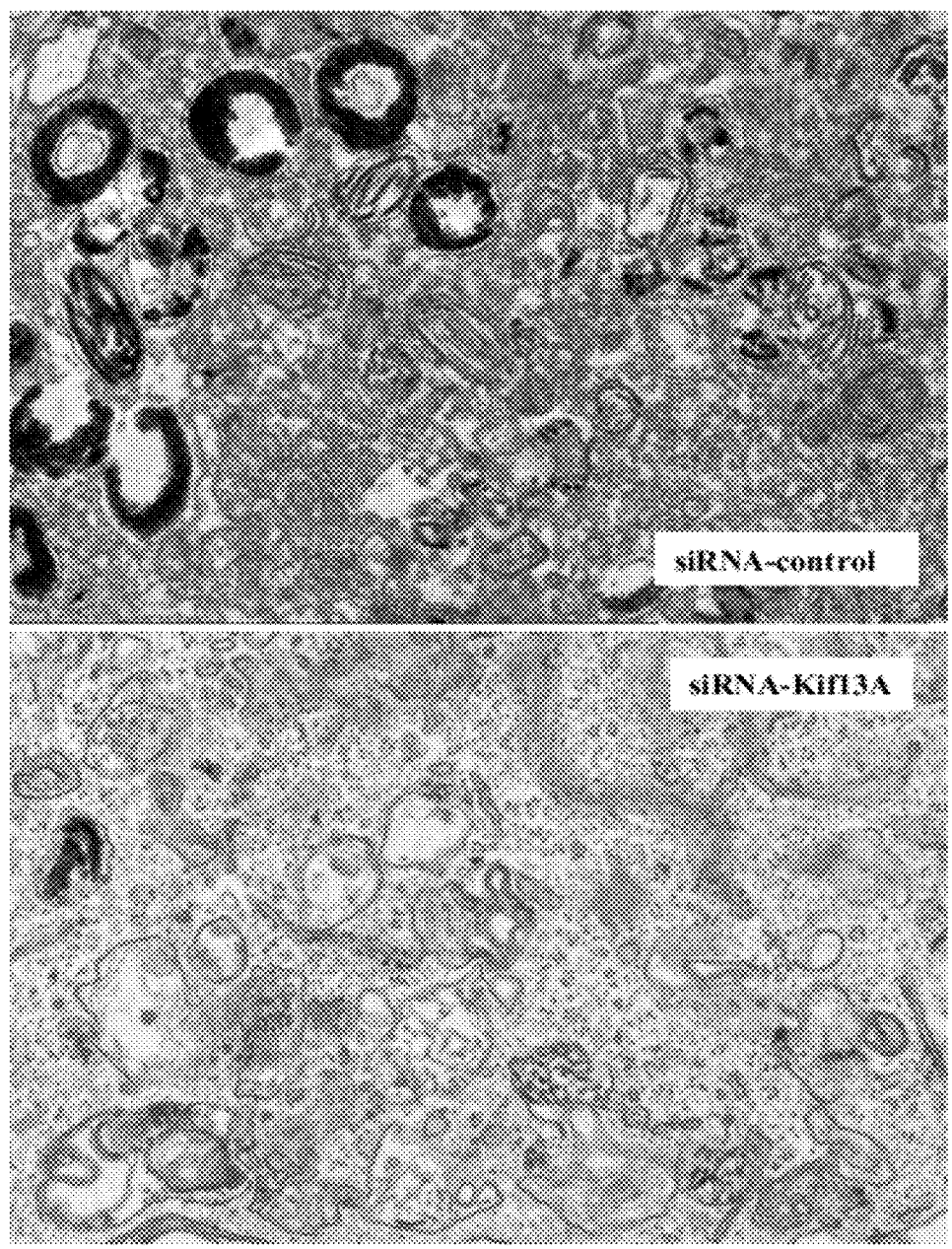
FIG. 3 shows electron microscope photographs of sections of melanocytes transfected with siRNA-control or siRNA-Kif13A.

The experiments of conventional electronic microscopy made it possible to show that melanocytes transfected with siRNA-control contained many melanosomes with large quantities of melanin (in black on FIG. 3). On the other hand, melanocytes transfected with siRNA-Kif13A contained no or few pigments.

In the cells transfected with siRNA-control, immunostaining revealed many mature stage III or IV melanosomes concentrating Tyrp1 proteins. On the other hand, with the cells transfected with siRNA-Kif13A, no mature melanosomes were visible and the Tyrp1 enzyme was dispersed in vesicular structures with endosome characteristics.

Thus, the inactivation of kinesin Kif13A disturbs the transfer of the enzymes of the melanogenesis in the pre-melanosomes and thus blocks the maturation of these organelles which are, consequently, unable to ensure the synthesis of melanin Conclusion The results obtained by these experiments firstly made it possible to observe that the use of specific siRNA inactivates kinesin Kif13A in melanocytes.

The results obtained also show that the use of specific siRNA of kinesin Kif13A makes it possible to significantly decrease:

quantity of melanin produced in melanocytes,
quantity of melanocytes containing pigmented mature melanosomes, and,
the proportion of mature melanosomes (stage III or IV) in melanocytes.

By these experiments, the inventors thus showed that specific siRNA of a kinesin interacting with AP-1, and in particular of kinesin Kif13A, have a significant effect on the production of melanic pigments and can thus effectively be used as depigmentation agents.

Example 2

Figure 4:
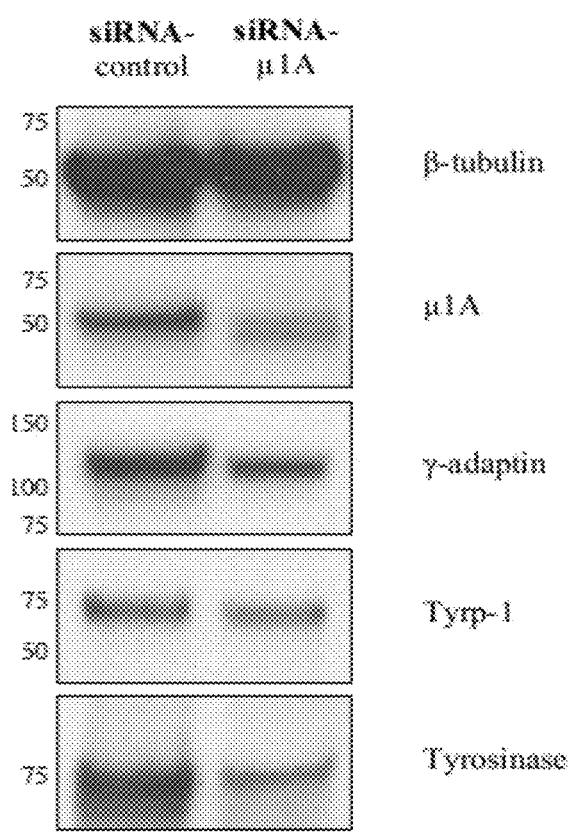
FIG. 4 presents the results obtained by western-blot experiments on protein extracts of melanocytes transfected with siRNA-control or siRNA-μ1A. The expression of μ1 and γ-adaptin sub-units of AP-1 complex is evaluated here quantitatively by using the β-tubulin expression level as reference.

The western blot experiments on transfected melanocytes (FIG. 4) made it possible to show that the expression of the μ1A sub-unit of AP-1 is strongly decreased in melanocytes transfected with siRNA-μ1A compared to those transfected with siRNA-control. This drop in expression also involved a decrease in the expression of another sub-unit of AP-1, γ-adaptin, with the consequence of destabilizing the AP-1 adaptor complex. These results thus confirm that the inactivation of only one sub-unit of AP-1 is enough to completely destabilize this complex. Moreover, it was observed in a surprising manner that in the cells transfected with siRNA-μ1A and thus deficient in AP-1, the expression of tyrosinase, a key enzyme of melanogenesis, was strongly decreased, as was the expression of Tyrp-1 enzyme although less strongly.

These results thus show that inactivation of only one sub-unit of AP-1 is enough to destabilize and inactivate the adaptor complex but also disturbs expression of the principal enzymes of melanogenesis.

Figure 5A:
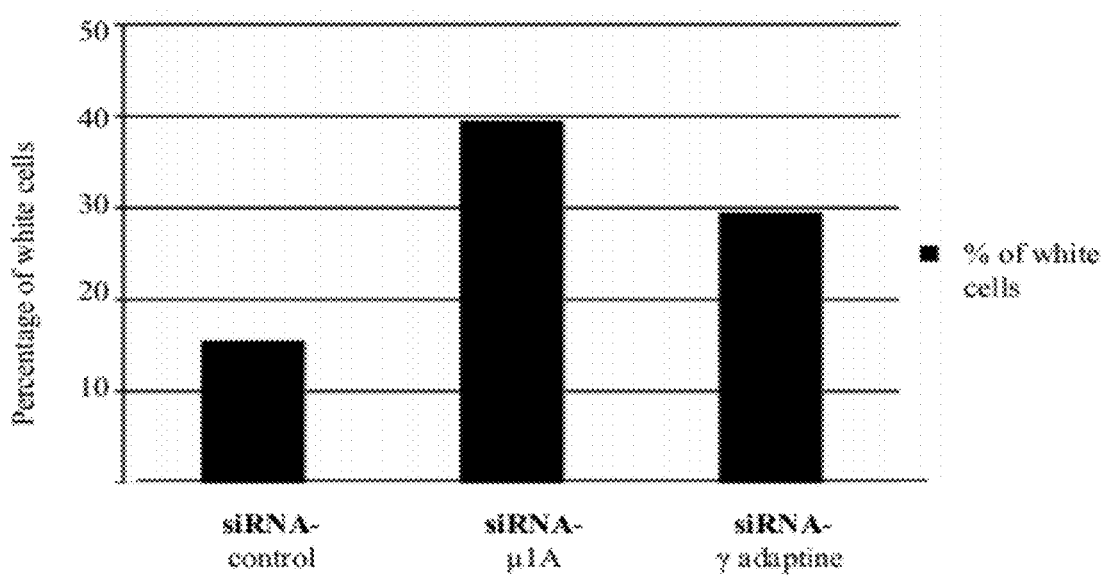
FIGS. 5A and 5B show diagrams presenting the percentages of white cells, i.e. melanocytes not containing a mature pigmented melanosome, among melanocytes transfected with siRNA-control, siRNA-μ1A or siRNA-γ-adaptin (FIG. 5A) or with the combination of siRNA-γ-adaptin and siRNA-μ1A (FIG. 5B). These measurements were taken by direct counting using an optical microscope (phase contrast).
Figure 5B:
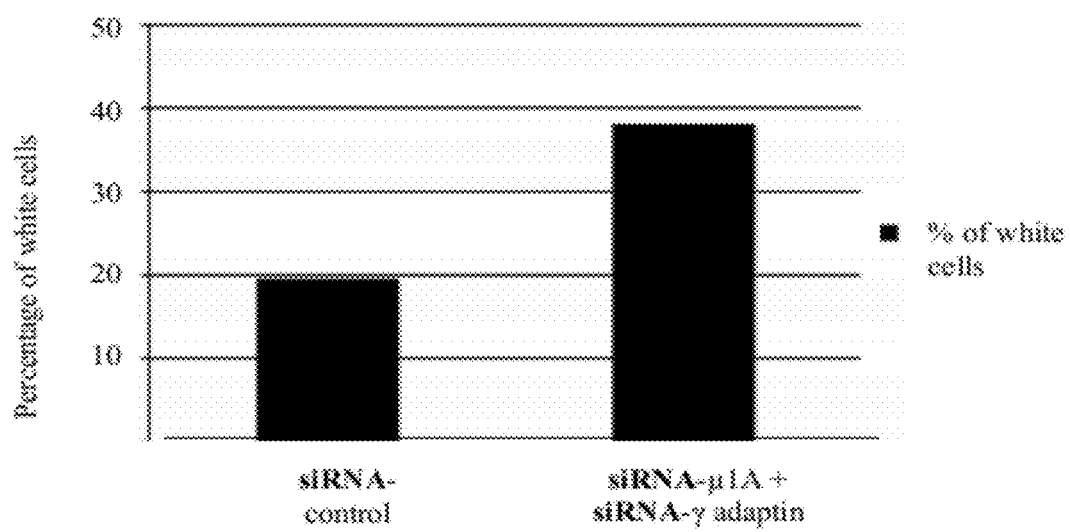
Figure 6:
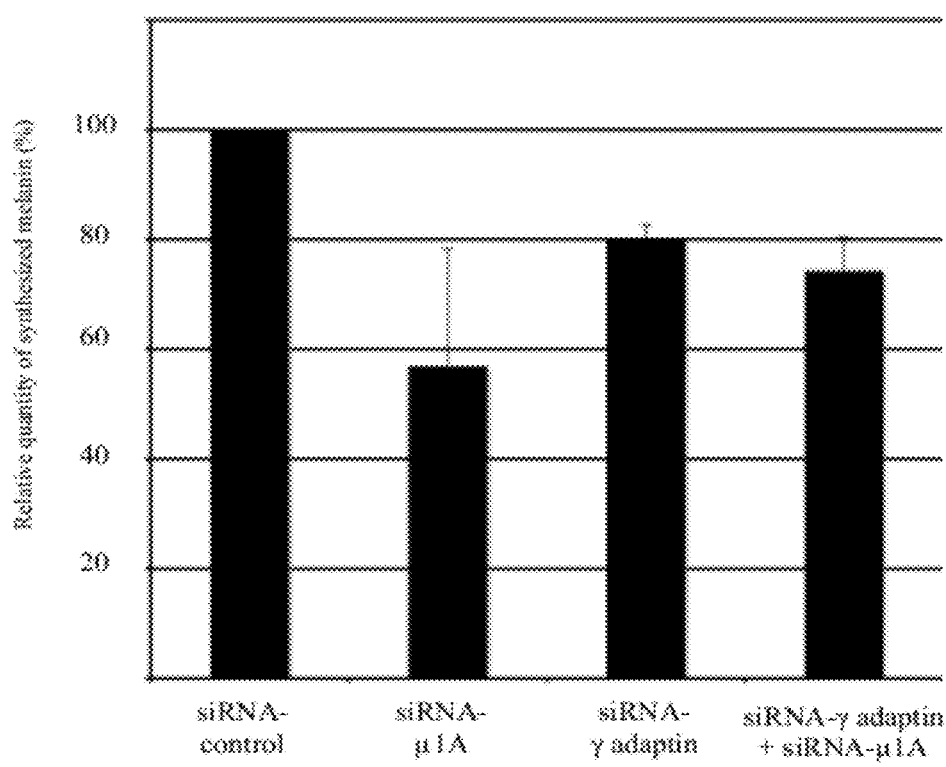
FIG. 6 shows a diagram presenting the percentage of melanin in melanocytes transfected with siRNA-control, siRNA-μ1A or the combination of siRNA-γ-adaptin and siRNA-μ1A. The quantity of melanin in melanocytes transfected with siRNA-control is regarded as being equal to 100%. The quantity of melanin was determined by measuring the optical density of the cell lysate at a wavelength of 492 nm.

Quantification of white cells, i.e. cells not containing a pigmented mature melanosome, among the transfected melanocytes, was carried out by direct counting under optical microscopy (phase contrast) (FIGS. 5A and 5B) and the percentage of melanin in these cells compared to the quantity present in the cells transfected with siRNA-control was determined by measuring the optical density of the cell lysate at a wavelength of 492 nm (FIG. 6). FIGS. 5A, 5B and 6 show the results obtained on melanocytes transfected with siRNA-control, siRNA-1 μA, siRNA-γ-adaptin or a combination of siRNA-1 μA and siRNA-γ-adaptin. The results presented in FIGS. 5A and 5B show that the use of siRNA-1 μA, siRNA-γ-adaptin (FIG. 5A) or both simultaneously (FIG. 5B) made it possible to significantly increase the proportion of white cells among transfected melanocytes, by comparison with those transfected with siRNA-control. This increase reached 24% for the cells transfected with siRNA-1 μA alone. These results were confirmed by those presented in FIG. 6 where it appears that the transfection of siRNA-1 μA, siRNA-γ-adaptin or both simultaneously made it possible to decrease notably the quantity of melanin synthesized in the cells by comparison with those transfected with siRNA-control. This decrease could reach more than 40% in the cells transfected with siRNA-1 µA.

These results thus show that the inactivation of one or more sub-units of AP-1 complex by one or more siRNA makes it possible to significantly decrease the synthesis of melanin in melanocytes.

Observations under electronic microcopy were carried out on melanocytes transfected with siRNA-µ1A or siRNA-control either under conventional microscopy (FIG. 7) or with immunostaining with anti-Tyrp1 antibodies (data not shown).

Figure 7:
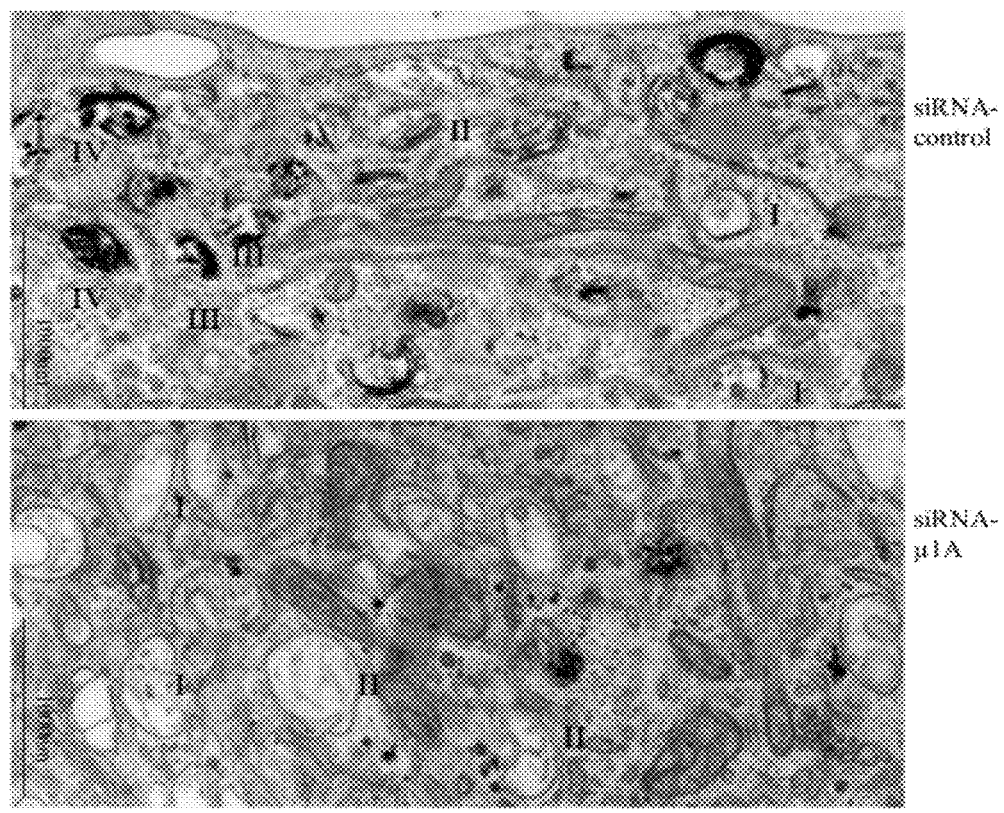
FIG. 7 shows electron microscope photographs of sections of melanocytes transfected with siRNA-control and with siRNA-μ1A. The Roman numerals on the photographs correspond to the stages of melanosome maturation present in the cell.

The experiments with conventional electronic microscopy made it possible to show that melanocytes transfected with siRNA-control contained many melanosomes with large quantities of melanin (in black on FIG. 7). On the other hand, melanocytes transfected with siRNA-µ1A contained no or few pigments.

In the cells transfected with siRNA-control, immunostaining revealed many mature stage III or IV melanosomes concentrating Tyrp1 proteins. On the other hand, the cells transfected with siRNA-µ1A, in which AP-1 adaptor complex was thus inactivated, contained only immature stage I or II melanosomes. No mature melanosomes were visible in these cells. The Tyrp1 enzyme was always detected by the antibody but was present only in vesicular structures with endosome characteristics and lacking pigment.

These observations thus indicate that the inactivation of AP-1 complex disrupts the transfer of the enzymes of melanogenesis in pre-melanosomes and thus blocks the maturation of these organelles which are, consequently, unable to ensure the synthesis of melanin.

Conclusion

The results obtained by these experiments first of all made it possible to observe that the use of specific siRNA inactivates AP-1 complex in melanocytes. Moreover, it was shown that inactivation of only one sub-unit of AP-1 adaptor complex is enough to destabilize and thus inactivate said complex.

The results obtained also show that the use of specific siRNA of a sub-unit of AP-1 adaptor complex makes it possible to decrease significantly:
quantity of melanin produced in melanocytes,
quantity of melanocytes containing pigmented mature melanosomes, and,
the proportion of mature (stage III or IV) melanosomes in melanocytes.

By these experiments, the inventors thus showed that specific siRNA of a sub-unit of AP-1 adaptor complex have a significant effect on the production of melanic pigments and can thus effectively be used as depigmentation agents.

REFERENCES

Ausubel et al., 1995, Current Protocols in Molecular Biology, Greene Publishing and Wiley-Interscience.
Braun et al., 2007, Mol. Biol. Cell, 18, 4921-4931.
M. Egholm et al., 1992, J. Am. Chem. Soc, 114, 1895-1897.
Fanning and Symonds, 2006, RNA Towards Medicine, Handbook of Experimental Pharmacology, ed. Springer.
Kumar et al, 1993, Microbiol. Mol. Biol. Rev, 62, 1415-1434.
Maniatis et al., 1982, Molecular cloning, A laboratory Manual, Cold Spring Harbor.
Nakagawa et al., 2000, Cell, 103, 569-581.
Osborne et al. Aptamers as therapeutic and diagnostic reagents: problems and prospects. Curr Opin Chem Biol. 1997 June; 1(1):5-9
Raposo et al., 1997, Immunogold labeling of ultrathin cryo-sections: application in immunology. In: Handbook of Exp. Immunol., vol. 4, eds. L. A. Herzenberg, D. Weir, L. A. Herzenberg, and C. Blackwell, Cambridge, Mass.: Blackwell Science, Inc., 1-11
Raposo et al., 2001, J. Cell Biol. 152, 809-824.
Sambrook et al., 1989, Molecular cloning, A laboratory Manual, Cold Spring Harbor.
Seiji et al., 1963, Nature, March 16; 197:1082-4.
Theos et al., 2005, Mol. Biol. Cell, 16, 5356-5372.
Van Den Bossche et al., 2006, Traffic, 7, 769-778.

We claim:

1. A method for treating hyperpigmentation comprising administering to a subject having hyperpigmentation, a composition comprising at least one inhibitor selected from the group consisting of a kinesin Kif13A inhibitor, an inhibitor of a sub-unit of AP-1 adaptor complex, and an inhibitor of the interaction between a sub-unit of AP-1 adaptor complex or the AP-1 adaptor complex and kinesin Kif13A in an amount effective to treat hyperpigmentation, wherein said inhibitor is an antibody, a nucleic acid or a dominant negative peptide.

2. The method of claim 1, wherein said inhibitor is a kinesin Kif13A inhibitor.

3. The method of claim 1, wherein said inhibitor is an inhibitor of a sub-unit of AP-1 adaptor complex.

4. The method of claim 1, wherein said inhibitor is an inhibitor of the interaction between a sub-unit of AP-1 adaptor complex or the AP-1 adaptor complex and kinesin Kif13A.

5. The method of claim 1, wherein said inhibitor is an antibody.

6. The method of claim 1, wherein said inhibitor is a nucleic acid.

7. The method of claim 6, wherein said inhibitor is a nucleic acid comprising a sequence able to hybridize specifically with a gene or mRNA encoding a AP-1 adaptor complex sub-unit or encoding kinesin Kif13A and to decrease or suppress the expression of said the AP-1 adaptor complex sub-unit or kinesin Kif13A.

8. The method of claim 7, wherein said nucleic acid is an antisense oligonucleotide or an iRNA.

9. The method of claim 7, wherein said nucleic acid is an siRNA.

10. The method of claim 7, wherein said nucleic acid has a sequence of 15 to 50 nucleotides.

11. The method of claim 7, wherein said nucleic acid has a sequence of 15 to 30 nucleotides.

12. The method of claim 7, wherein said nucleic acid comprises a sequence selected from the group consisting of SEQ ID NO: 1, 2, 3, 4, 5, 6, 11, 12, 13, 14, 15, 16, 17, 18, 19, 20, 21, 22, 23 and 24.

13. The method of claim 1, wherein said inhibitor is a dominant negative peptide.

14. The method of claim 13, wherein said dominant negative peptide is only made up of the tail of a kinesin interacting with the AP-1 adaptor complex.

15. The method of claim 14, wherein said kinesin interacting with the AP-1 adaptor complex is kinesin Kif13A.

16. The method of claim 1, wherein said composition further comprises one or more active substances selected from the group consisting of ellagic acid; arbutin; resorcinol; vitamin C; pantothenate; kojic acid; placental extracts; molecules interfering directly or indirectly with melanotropin (MSH), its receptor or adrenocorticotropic hormone (ACTH); polyols; vitamins; keratolytic and/or exfoliating agents; alpha-hydroxy acids; ascorbic acid; retinoic acid; retinaldehyde; retinol; palmitate, propionate or acetate; anti-glycation and/or antioxidant agents; anti-inflammatory agents; soothing agents and mixtures thereof; chemical or physical sun filters; deoxyribonucleic acids, and ribonucleic acids.

17. The method of claim 16, wherein said anti-glycation and/or antioxidant agents are tocopherol, thiotaurine, hypotaurine, aminoguanidine, thiamin pyrophosphate, pyridoxamine, lysine, histidine, arginine, phenylalanine, pyridoxine or adenosine triphosphate.

18. The method of claim 1, wherein said composition is topically administered to the subject.

19. The method of claim 1, wherein said composition is a pharmaceutical composition.

20. The method of claim 1, wherein said composition is a cosmetic composition.

21. A method for reducing hyperpigmentation comprising administering to a subject a composition comprising at least one inhibitor selected from the group consisting of a kinesin Kif13A inhibitor, an inhibitor of a sub-unit of AP-1 adaptor complex, and an inhibitor of the interaction between a sub-unit of AP-1 adaptor complex or the AP-1 adaptor complex and kinesin Kif13A, wherein said inhibitor is an antibody, a nucleic acid or a dominant negative peptide.

* * * * *

UNITED STATES PATENT AND TRADEMARK OFFICE
CERTIFICATE OF CORRECTION

| | | |
|---|---|---|
| PATENT NO. | : 8,669,238 B2 | Page 1 of 1 |
| APPLICATION NO. | : 13/569576 | |
| DATED | : March 11, 2014 | |
| INVENTOR(S) | : Graca Raposo et al. | |

It is certified that error appears in the above-identified patent and that said Letters Patent is hereby corrected as shown below:

In the Specification

<u>Column 16,</u>
Line 21, "Labvisio®);" should read --Labvision®);--.

Signed and Sealed this
Tenth Day of February, 2015

Michelle K. Lee
*Deputy Director of the United States Patent and Trademark Office*